(12) United States Patent
Chang et al.

(10) Patent No.: US 8,835,179 B2
(45) Date of Patent: Sep. 16, 2014

(54) REAL-TIME MONITOR SOLID PHASE PEPTIDE SYNTHESIS BY MASS SPECTROMETRY

(75) Inventors: Li-Chiao Chang, Kaohsiung (TW); Jentaie Shiea, Tainan County (TW); Yi-Tzu Cho, Kaohsiung (TW)

(73) Assignees: ScinoPharm Taiwan, Ltd., Shan-Hua (TW); National Sun Yat-Sen University, Kaohsiung (TW)

( * ) Notice: Subject to any disclaimer, the term of this patent is extended or adjusted under 35 U.S.C. 154(b) by 0 days.

(21) Appl. No.: 13/284,837

(22) Filed: Oct. 28, 2011

(65) Prior Publication Data

US 2012/0107941 A1 May 3, 2012

Related U.S. Application Data

(60) Provisional application No. 61/408,072, filed on Oct. 29, 2010.

(51) Int. Cl.
*G01N 27/72* (2006.01)
*G01N 33/68* (2006.01)

(52) U.S. Cl.
CPC .................................. *G01N 33/6848* (2013.01)
USPC ........................................................... 436/86

(58) Field of Classification Search
CPC ..................................................... G01N 27/72
USPC ........................................................... 436/86
See application file for complete search history.

(56) References Cited

U.S. PATENT DOCUMENTS

| 6,278,111 | B1 | 8/2001 | Sheehan et al. | |
|---|---|---|---|---|
| 6,677,114 | B1 * | 1/2004 | Schneider et al. | 435/4 |
| 2007/0176113 | A1 * | 8/2007 | Shiea et al. | 250/423 P |
| 2008/0116366 | A1 * | 5/2008 | Shiea et al. | 250/282 |
| 2008/0272294 | A1 | 11/2008 | Kovtoun | |
| 2008/0308722 | A1 | 12/2008 | Shiea | |

FOREIGN PATENT DOCUMENTS

| CN | 1270598 A | 10/2000 |
|---|---|---|
| CN | 101173914 A | 5/2008 |
| EP | 1 918 974 A2 | 5/2008 |
| GB | 2 410 370 A | 7/2010 |
| TW | I271771 B | 10/2007 |
| WO | 99/05319 A2 | 2/1999 |

OTHER PUBLICATIONS

Fitzgerald, et al., "Direct characterization of solid phase resin-bound molecules by mass spectrometry," Bioorganic & Medicinal Chemistry Letters, 1996, vol. 6, pp. 979-982.
Maux et al., "Static Secondary Ino Mass Spectrometry to Monitor Solid-Phase Peptide Synthesis," Journal of the American Society for Mass Spectrometry, 2001, vol. 12, pp. 1099-1105.
McKeown et al., "A photolabil carbamate based dual linker analytical construct for facile monitoring of solid phase chemistry," Tetrahedron Letters, 1999, vol. 40, pp. 2407-2410.
International Search Report and Written Opinion, mailing date Jun. 12, 2012; PCT application No. PCT/IB2011/002547, 8 pages.
Cheng et al., "Electrospray-Assisted Laser Desorption/Ionization Mass Spectrometry for Continuously Monitoring the States of Ongoing Chemical Reaction in Organic or Aqueous Solution under Ambient Conditions," Anal. Chem., 2008, vol. 80, pp. 7699-7705.
Chipuk et al., "The Influence of Material and Mesh Characteristics on Transmission Mode Desorption Electrospray Ionization," J. Am. Soc. Mass Spectrom, 2009, vol. 20, pp. 584-592.
Huang et al., "Effects of matrix, electrospray solution, and laser light on the desorption and ionization mechanisms in electrospray-assisted laser desorption ionization mass spectrometry," Analyst, 2010, vol. 135, pp. 759-766.
EP Application No. 11835703.7, Supplemental European Search Report, Mar. 4, 2014, 8 pages.

* cited by examiner

*Primary Examiner* — Christine T Mui
(74) *Attorney, Agent, or Firm* — Kilpatrick Townsend & Stockton LLP; William B. Kezer

(57) ABSTRACT

Provided are systems, apparatus, materials and methods for directly monitoring products and intermediates of solid phase chemical synthesis such as solid phase peptide synthesis.

17 Claims, 11 Drawing Sheets

6 mer (a)

(b)

(c)

Schematic representation of the MS detection of peptide molecules conjugated on solid phase supports.

REAL-TIME MONITOR SOLID PHASE PEPTIDE SYNTHESIS BY MASS SPECTROMETRY

CROSS-REFERENCES TO RELATED APPLICATIONS

This application claims priority from U.S. Provisional Patent Application Ser. No. 61/408,072 which was filed on Oct. 28, 2010. The entire content of U.S. Provisional Patent Application Ser. No. 61/408,072 is incorporated herein by reference in its entirely.

FIELD OF THE INVENTION

The present disclosure provides systems and methods for real-time monitoring of solid phase peptide synthesis (SPPS) under ambient atmosphere for characterizing peptide intermediates or products on-line. The present disclosure also demonstrates the capability of this real-time monitoring system for tracing the process of step reactions of SPPS. In other embodiments, the present disclosure provides a sample plate for loading solid sample that can influence the analytical stability and sensitivity of laser desorption and electrospray ionization mass spectrometry.

BACKGROUND OF THE INVENTION

Combinatorial chemistry is a technology for simultaneously creating and rapidly screening a large number of different compounds r to identify useful compounds. Such peptide libraries can be used for the screening enzymatic substrates and inhibitors or cell binding peptides. Unlike the conventional synthetic way of handling one type of molecule at a time, combinatorial chemistry is an important tool for the discovery of new drug candidates, catalysts, and materials. Currently, several hundred peptide-based drugs have entered clinical phase testing or have already been commercialized, since peptides are considered as highly potent drug candidates due to their high specificity and low toxicity. Accordingly, the demand for the production of peptides in large quantities has also increased, and chemical synthesis methods using combinatorial chemistry play an important role.

Among various chemical synthesis methods, a solid phase peptide synthesis (SPPS) method, first described by Merrifield in 1963, has become a major breakthrough for the development of combinatorial chemistry due to its simplified reaction procedure and easy purification/isolation steps for the target products. The first amino acid is bounded to an insoluble support consisting of either resins or plastic pins and the desired sequence is built step by step by successive couplings of the appropriate protected amino acids. Reactions can be moved to completion by the use of excess reagents and repeated washings for purification. The methodology allows for automated peptide preparation relying on efficient chemistries without redundant and time consuming purification procedures. As a result, the synthesis of combinatorial libraries using solid phase chemistry has now become a routine strategy in the practice of drug discovery.

However, there are still a number of shortcomings associated with the use of solid phase chemistry, particularly in its analysis. Although mass spectrometry can offer high throughput analysis for combinatorial libraries, too many molecules do not have appropriate ionization properties for this technique to be universally applicable. Moreover, on-line monitoring of the multi-step synthesis using standard spectroscopic methods requires solubilization of the sample under study that is free from its solid support. Compound determination is thus usually achieved at the end of the synthesis since it is at this stage that the peptide is released from the insoluble support into solution. Utilizing such a cleavage and analysis strategy as a means of quality control and reaction monitoring presents several drawbacks. This type of compound assessment at an intermediate stage is destructive, as samples are consumed. Side-reactions with the cleavage reagents during this additional cleavage step may occur, leading to difficulties in the determination of peptides products by MS (mass spectrometry) due to the complicated mass spectra that are obtained.

Several reports (Michael C. F. et al., *Bioorganic & Medicinal Chemistry Letters*, Vol. 6, 979-982, 1996; Stephen C. M. et al., *Tetrahedron Letters*, Vol. 40, 2407-2410, 1999) have shown that matrix-assisted laser desorption ionization-time of flight mass spectrometry (MALDI-TOF) could be used to analyze selected Fmoc-protected amino acids or peptides bound to a solid-phase resin through a photolabile linker. Some other articles (Delphine M. et al., *Journal of the American Society for Mass Spectrometry*, Vol. 12, 1099-1105, 2001) reported that time-of-flight secondary ion mass spectrometry (TOF-S-SIMS) could be utilized to characterize analytes anchored to solid supports in a single step requiring no pretreatment of the sample. However, desorption and ionization in both MALDI-TOF and TOF-S-SIMS must be performed in high vacuum system. Monitoring solid phase peptide synthesis in real time for synthesis quality control is not possible with these kinds of techniques.

Development of a direct non- or minimally destructive on-line monitoring method would allow peptide solid-phase synthesis to be followed step by step for good quality control. The present disclosure provides such methods and addresses some of the limitations noted above.

BRIEF SUMMARY OF THE INVENTION

The present disclosure provides in one embodiment a real-time monitor SPPS system under ambient atmosphere so as to characterize peptide intermediates or products on-line, i.e. that are bound to a solid support. Solid phase synthesis samples are dispersed in organic solvents followed by exposure to a pulsed laser beam to break the chemical bonding between the peptide and solid support (such as a resin) and exposure to an electrospray plume for ionization towards a mass spectrometer (see FIG. 11). The inventors have found this strategy to be applicable, for example to resin-connected peptides products for successfully directly analyzing peptide molecules by mass spectrometry without any sample pretreatment or acid cleavage.

DETAILED DESCRIPTION OF THE INVENTION

Figure 1:
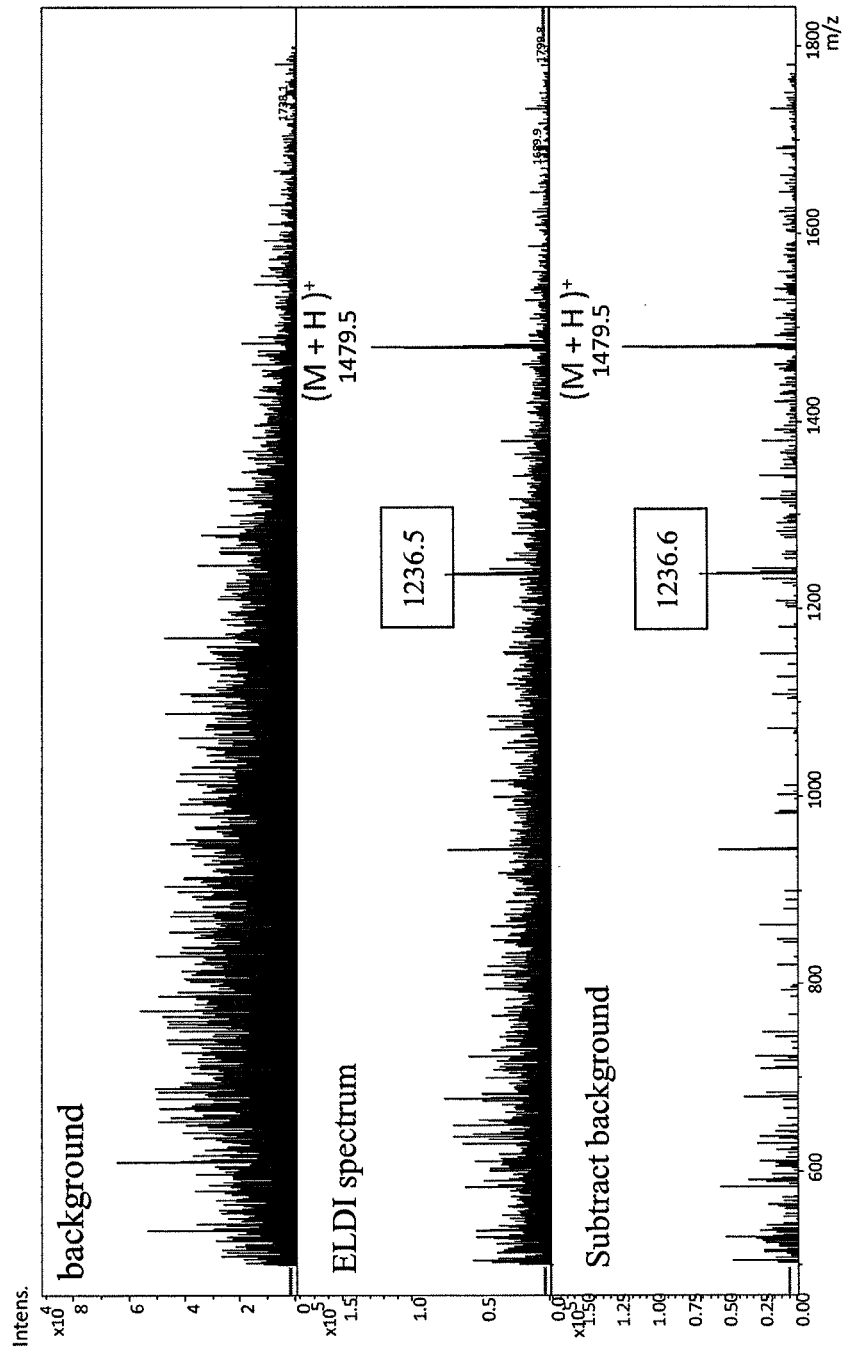
FIG. 1 provides a positive mass spectrum of sample 1 dispersed in organic solvent (dichloromethane). The samples in liquid solvent exposed to a pulsed laser beam and electrospray capillary for ionization and analyzed by an ion trap.
Figure 2:
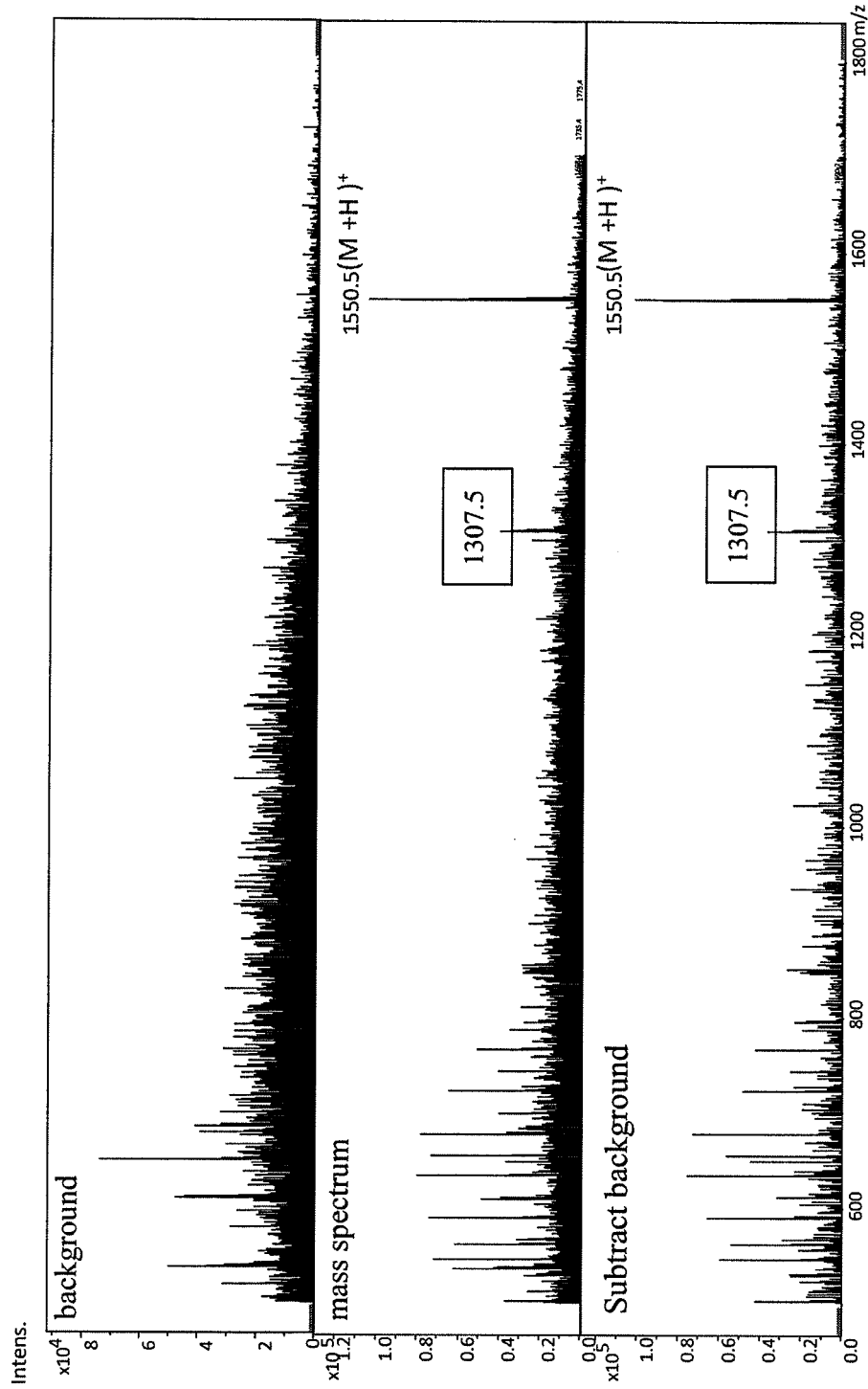
FIG. 2 provides a positive mass spectrum of sample 2 dispersed in organic solvent (dichloromethane). The samples in liquid solvent exposed to a pulsed laser beam and electrospray capillary for ionization and analyzed by an ion trap.
Figure 3:
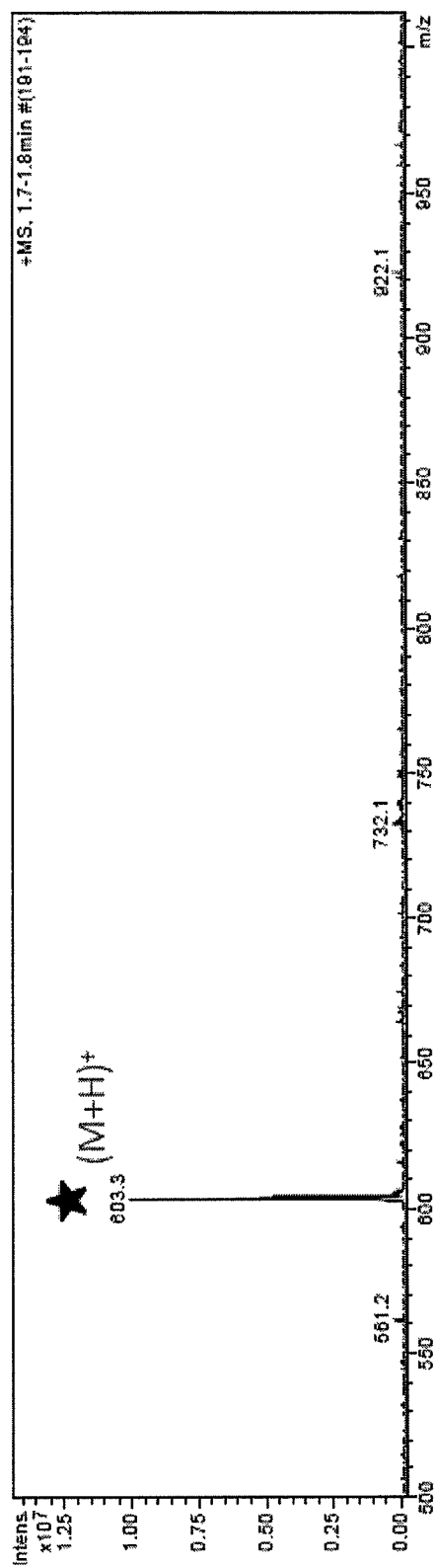
FIG. 3 provides a positive mass spectrum of sample 3 (4 mer de-Fmoc) dispersed in organic solvent (dichloromethane). The samples in liquid solvent exposed to a pulsed laser beam and electrospray capillary for ionization and analyzed by an ion trap.
Figure 4:
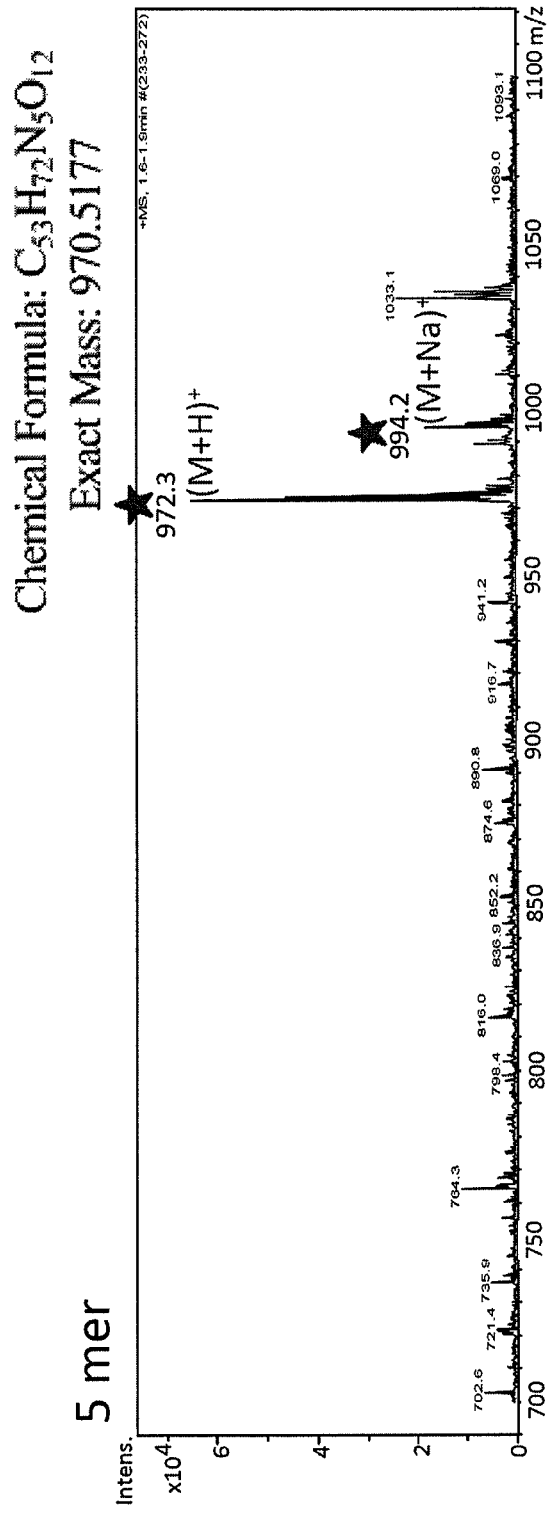
FIG. 4 provides a positive mass spectrum of sample 4 (5 mer) dispersed in organic solvent (dichloromethane). The samples in liquid solvent exposed to a pulsed laser beam and electrospray capillary for ionization and analyzed by an ion trap.
Figure 5:
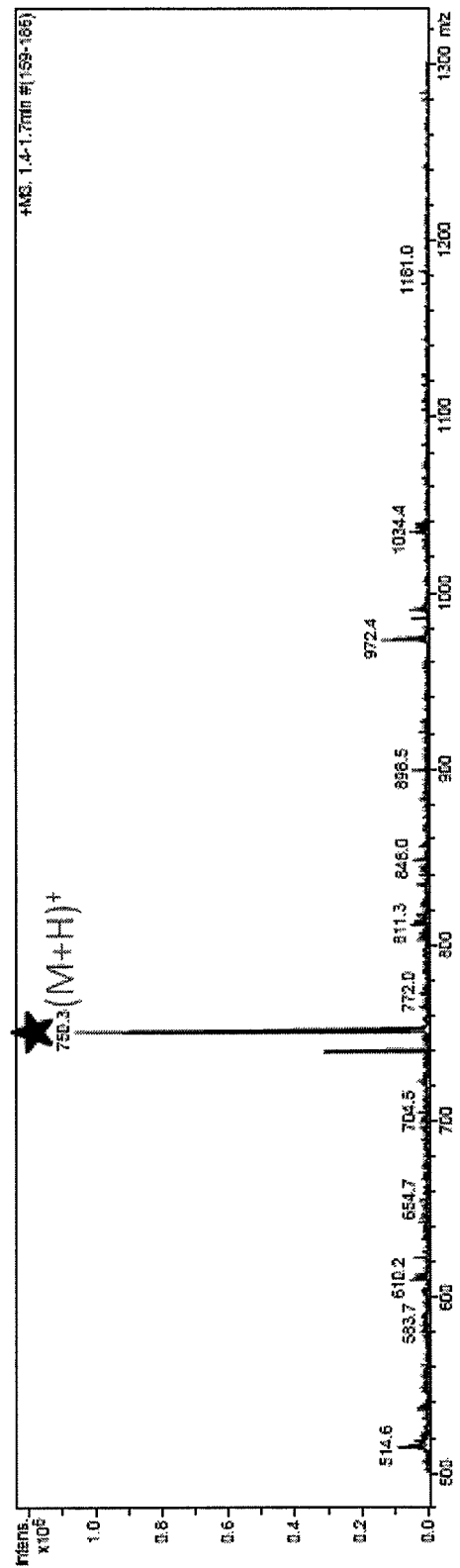
FIG. 5 provides a positive mass spectrum of sample 5 (5 mer de-Fmoc) dispersed in organic solvent (dichloromethane). The samples in liquid solvent exposed to a pulsed laser beam and electrospray capillary for ionization and analyzed by an ion trap FIG. 6 provides a positive mass spectrum of sample 6 (6 mer) dispersed in organic solvent (dichloromethane). The samples in liquid solvent are exposed to a pulsed laser beam and electrospray capillary for ionization and analyzed by an ion trap.
Figure 6:
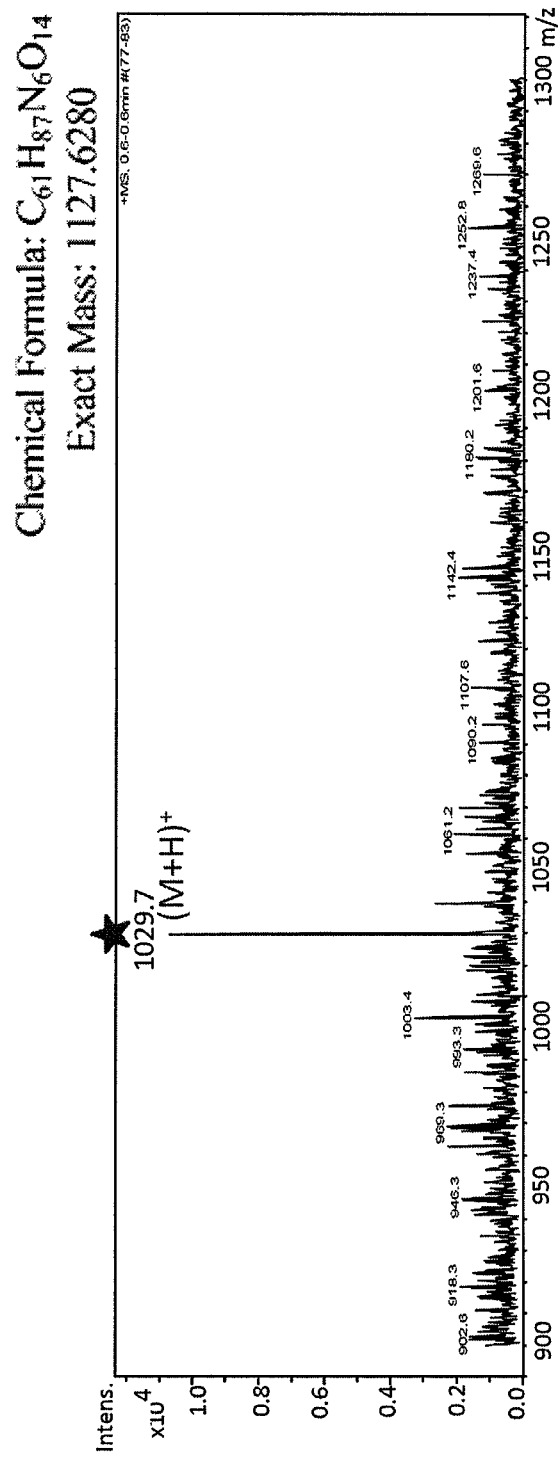

One embodiment of the present disclosure provides a vital analytical method to directly detect the peptides synthesized on a solid support. In some aspects, the solid support is a resin. One of skill in the art will appreciate that a variety of support materials are useful in the process and with the systems described herein, though some supports are preferred such as terephthalate resins. Other than the use of an organic solvent to disperse the resin-peptides samples, no other sample pre-treatments are required before the MS detection. When using conventional destructive analytical methods to characterize masses of compounds on the solid supports, acid hydrolysis or acid cleavage of the peptide molecules is necessary to separate the molecules from the insoluble resin. As a consequence, side-reactions such as de-blocking or de-protecting cause additional fragments to form in the system, and determination of the intermediates or products becomes confusing and difficult. Unlike these acid release methods, the molecular weight information of the intact peptide molecules can be obtained in this direct analysis system, and sample consumption is also greatly reduced. Moreover, this strategy allows for analysis under an ambient environment that is more straightforward for real-time monitor reaction and quality control than those techniques in high vacuum system. This direct minimally destructive on-line monitoring method allows peptide solid-phase synthesis to be followed step by step for improved quality control.

In one embodiment, a system is provided for real-time monitoring of a chemical reaction comprising:
a) a sample;
b) a solvent exchange reservoir;
c) a light source;
d) an electrospray unit, and
e) a mass spectrometer.

While the nature of the sample shown herein is for peptide synthesis, the systems can be used for monitoring a variety of chemical synthesis strategies that occur on solid supports in a step-wise fashion. As noted above, the systems described herein also provide a solvent exchange reservoir to facilitate contacting the sample with solvent and the light source (typically a laser). The solvent is typically a lower boiling point solvent that is non-reactive under the conditions of the real-time monitoring. The solvent exchange reservoir can be integrated into the system for automated solvent release onto the sample (and support), or it can be removed from the system such that solvent is added manually to the sample/support. The light source is typically a laser to provide focused light to a sample site. A variety of lasers are useful, including a Nd-YAG laser (266-1064 nm, 20 Hz) such as a Lotis-Tii LS-2130 with a high voltage power supply (0-30 KV, 0-300 µA, Spellman CZE1000PN30) as well as other comparable laser light sources. The electrospray unit and mass spectrometer are described below (and include models such as the Ion-trap Mass Spectrometer Esquire 3000 plus by Bruker).

In one embodiment, a method is provided for real-time monitoring of a chemical reaction using a mass spectrometer, said method comprising the steps of:
a) providing a sample in/from a container where the chemical synthesis occurs;
b) subjecting the synthesized sample to an organic solvent;
c) using a light source to break a chemical bonding and transport the analyte molecules in a electrospray ionization plume; and
d) analyzing the precursor ion spectrum of the analyte molecules to determine the molecular weight of synthesis products.

In one embodiment, provided is method for real-time monitoring of solid phase peptide synthesis using a mass spectrometer, said method comprising the steps of:
a) providing a peptide on resin in/from a container where the chemical synthesis occurs;
b) subjecting the synthesized peptide on a plate, to an organic solvent;
c) using a light source to break a chemical bonding and transport the analyte molecules in a electrospray ionization plume; and
d) analyzing the precursor ion spectrum of the analyte molecules to determine the molecular weight of synthesis products.

In one embodiment chemical reaction is conducted in a chemical synthesis reactor. Chemical reactions include peptide synthesis. In some such embodiments the peptide synthesis is solid phase peptide synthesis. Any number of solid supports may be employed, including resins such as polystyrene and polyamide based resins. The peptides are covalently bound to a solid support, typically at their C-terminal end through linkers such as acid labile and photolabile linkers. In some embodiments the linker is an acid labile linker. In other embodiments, the linker is a trityl linker such as a 2-chlorotrityl linker. Peptide synthesis is typically performed by coupling a protected amino acid to the N-terminal end of the bound sample. The protected amino acid may contain N-terminal protecting groups such as a Boc (tert-butyloxycarbonyl) or Fmoc (9-fluorenylmethyloxycarbonyl), group as well as side chain protecting groups.

In some embodiments, the sample or chemical synthesis reactor, solvent exchange reservoir, light source, electrospray unit, and mass spectrometer analyzer form a single apparatus. In some aspects, the chemical synthesis reactor is in fluid communication with the solvent exchange reservoir. In other aspects, the reactor chamber and solvent exchange reservoir are the same, i.e. the reaction chamber is also the solvent exchange reservoir.

The solvent exchange reservoir contains a solvent for delivery to the reaction chamber, so that the sample is in contact with the solvent prior to exposure to the light source. In one embodiment the solvent is an organic solvent, including polar and non-polar organic solvents. In some aspects, the solvent is methylene chloride. In other aspects, the solvent is a polar protic solvent such as methanol. In one embodiment the solvent is substantially free from solid matrices or crystallizable low molecular weight organic molecules that are capable of sublimation and/or transferring charge to the sample upon exposure to the light source such as those matrices employed in MALDI (matrix assisted laser desorption ionization). These low molecular weight matrices include those that having molecular weights less than 1000, 500, 400, or 300 grams/mole and include 3,5-dimethoxy-4-hydroxycinnamic acid (sinapinic acid), α-cyano-4-hydroxycinnamic acid (alpha-cyano or alpha-matrix) and 2,5-dihydroxybenzoic acid (DHB).

The light source, electrospray unit, and mass spectrometer are all proximal to the chemical synthesis reactor and to each other. The light source is positioned to deliver light to the reaction chamber. In some embodiments the reaction chamber is located in the path of the electrospray plume generated by the electrospray unit. In some embodiments the electrospray plume is sprayed through the reaction chamber.

In the one embodiment, the light source is a laser such as a pulsed laser. The laser is of sufficient energy to cause cleavage of the covalent bond(s) between the sample and solid support to which it is attached. Upon cleavage, the resulting analyte molecules are exposed and swept up into an electrospray ionization plume originating from an electrospray unit.

The term "electrospray unit" and "electrospray emitter" is interchangeably in the present application. The electrospray unit can be in any number of shapes and can be in the form of a needle or capillary. The electrospay unit is conductive or contains an electrode. In some embodiments the mass spectrometer which contains a detector for ion mass detection also serves as the counter electrode to establish a voltage field relative to the electrospray unit. Liquid from the emitter is sprayed towards a mass spectrometer and is converted into an electrospray ionization plume comprising monodispersed droplets. Thus unlike conventional ESI (electrospray ionization) methods, the electrospray liquid of the present application prior to spraying is free of analytes, and the analytes are only incorporated after formation of the plume, which ionizes and transports the analyte to the mass spectrometer for detection and subsequent analysis.

The systems, materials, and methods disclosed herein are conducted at ambient pressure. The term ambient pressure as used herein refers to the natural air pressure found at a given elevation such as, for example, 760 mm Hg at sea level.

In one embodiment of the systems, apparatus, and materials disclosed herein, a plate is provided which is in contact with the sample prior to and during chemical synthesis. In other embodiments the plate is provided and placed in contact with the sample prior to exposure of the sample to the light source.

In some embodiments, the plate is a steel or polyester plate. In some aspects, the polyester is selected from polyethylene terephthalate. In other aspects the polyethylene terephthalate is black.

EXAMPLES

The following examples are provided for the purpose of further illustration only and are not intended to be limitations on the disclosed invention.

Example 1

Direct analyses of six solid phase peptides synthesis (SPPS) products (sample 1 to sample 6) dispersed in organic solvents were successfully performed by using laser desorption and electrospray ionization mass spectrometry without any sample pretreatment or acid cleavage. FIG. 1 to FIG. 6 show the mass spectra of the particle samples where the desired peptide chains were synthesized step by step on the support resin through a commonly used linker. The synthetic peptide molecules is easily characterized due to the molecule ions $[M+H]^+$ dominated in respective spectra.

Figure 7:
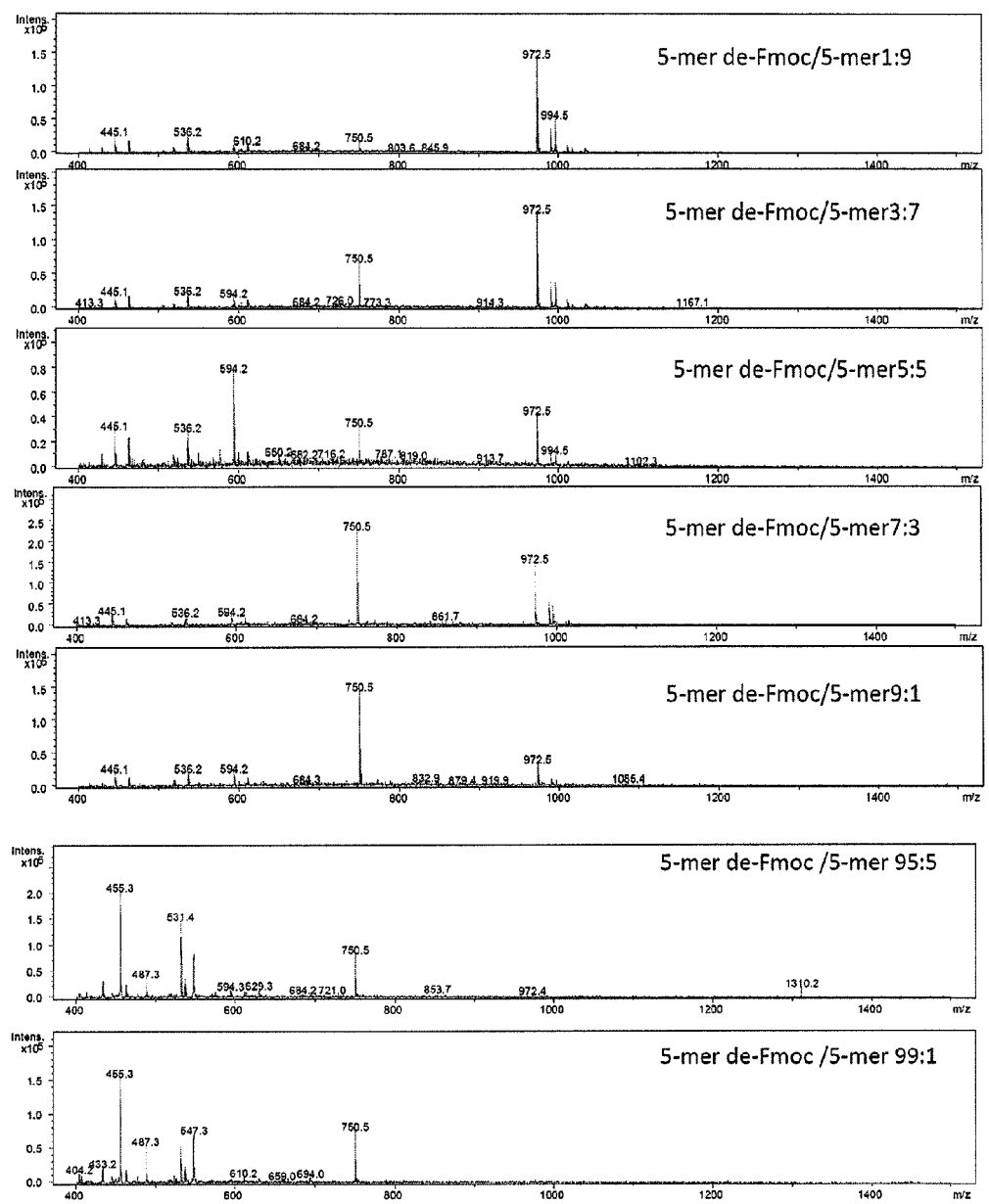
FIG. 7 provides a positive mass spectrum of mixed sample 5 (5 mer de-Fmoc) and sample 4 (5 mer) in different weight ratio (1:9 3:7, 5:5, 7:3, 9:1, 95:5, and 99:1).
Figure 8:
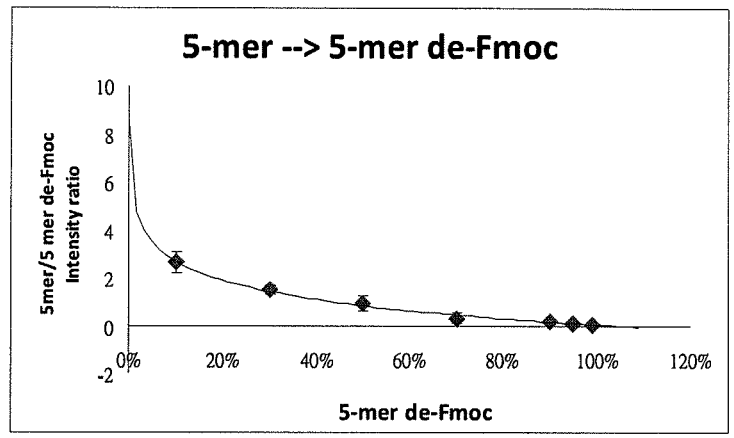
FIG. 8 provides a plot of the intensity ratio of 5 mer/5 mer de-Fmoc vs. 5 mer de-Fmoc weight percentage (a) 10%~99%; (b) 30%~90%; (c) 91%~99%.
Figure 8:
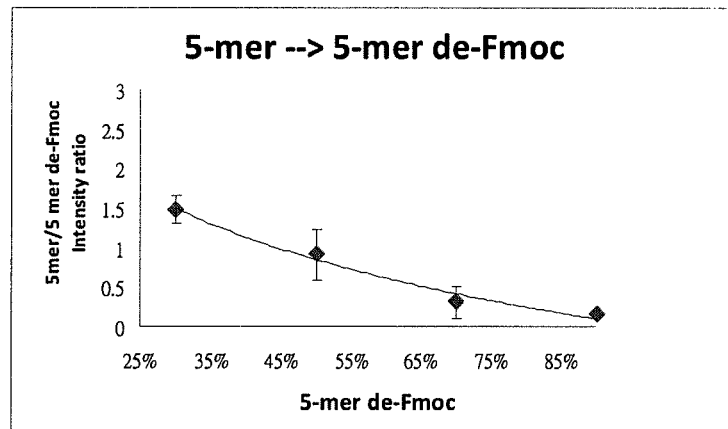
Figure 8:
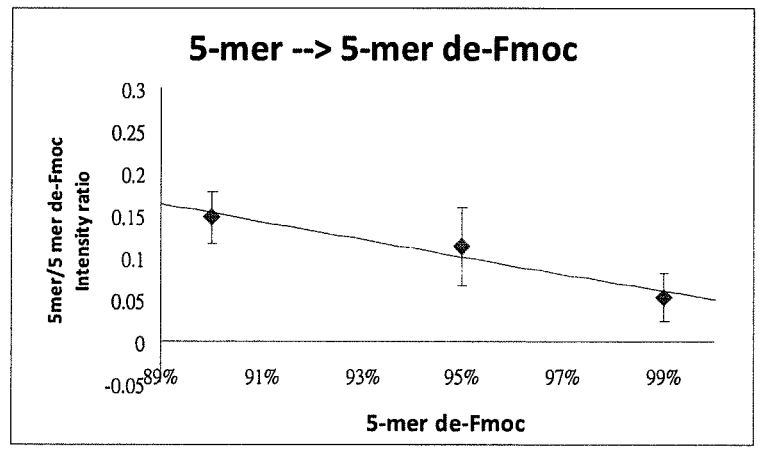

To demonstrate the capability of this real-time monitoring system for tracing the process of step reactions of SPPS, a simulative example of de-Fmoc step reaction (from 5mer molecule to 5mer de-Fmoc molecule) was also applied in this system. FIG. 7 shows positive mass spectra of samples mixed sample 5 (5mer de-Fmoc) and sample 4 (5mer) in different weight ratio (1:9, 3:7, 5:5, 7:3, 9:1, 95:5, and 99:1). The intensity of 5mer de-Fmoc (m/z 750.4) is increasing while that of 5mer (m/z 972.5) is decreasing according to the rising of 5mer de-Fmoc weight percentage in the de Fmoc progressing. FIG. 8 is the plot of the intensity ratio of 5mer/5mer de-Fmoc vs. 5 mer de-Fmoc weight percentage in different range. The down trend of intensity ratio of 5mer to 5mer de-Fmoc can still be traced even the weight percentage of 5mer is below 5% (that is 5mer de-Fmoc is above 95%). It indicates that this detection system can indeed be used to monitor SPPS reactions and judge the completion of reactions step by step.

Sample 1
Structure:
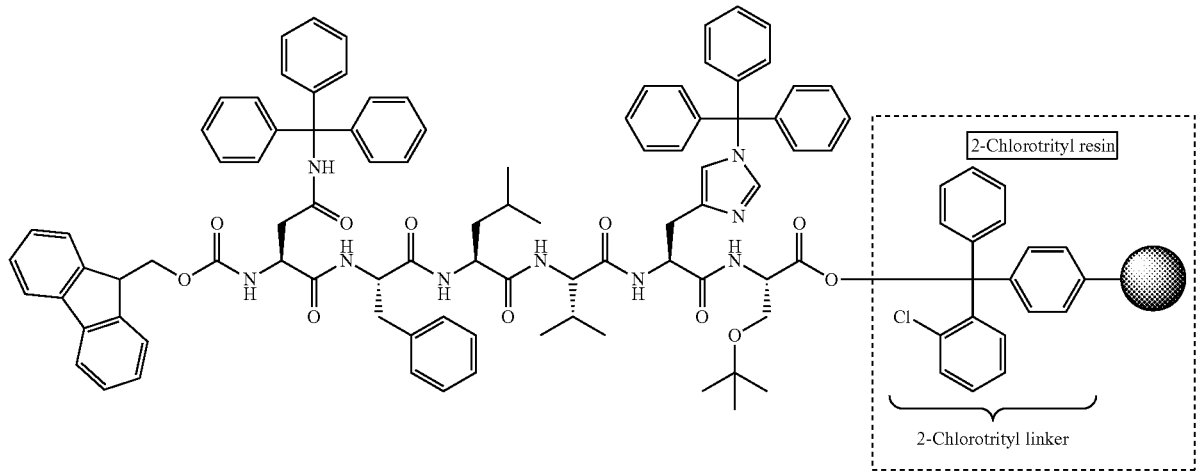
Chemical Formula: $C_{90}H_{94}N_9O_{11}$
Exact Mass: 1476.71
Molecular Weight: 1477.76
Sample 2
Structure:
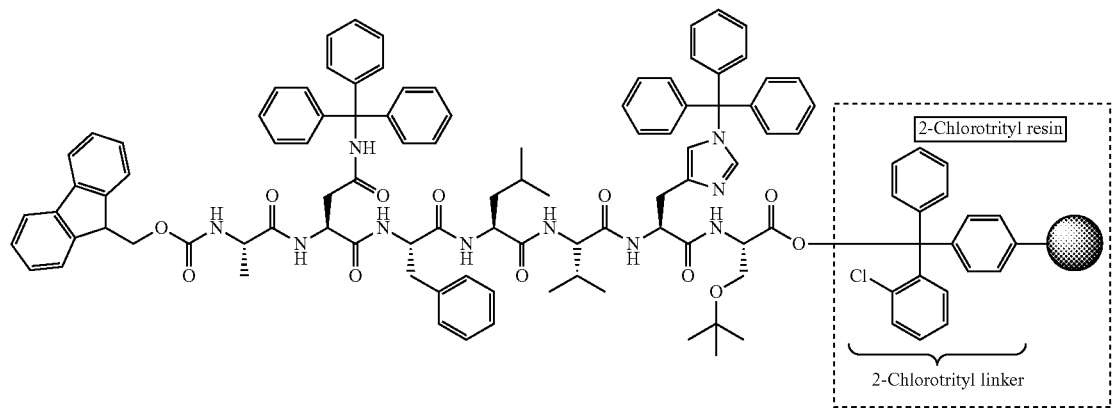
Chemical Formula: $C_{93}H_{99}N_{10}O_{12}$
Exact Mass: 1547.74
Molecular Weight: 1548.84

Sample 3 (4 mer de-Fmoc)
Structure:
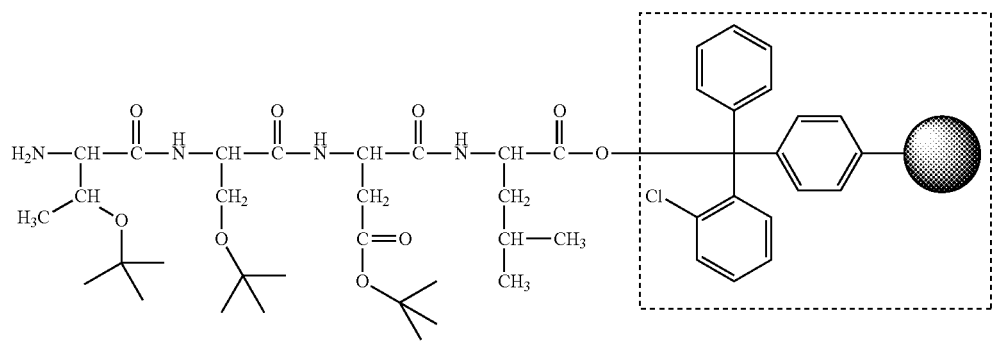
Chemical Formula: $C_{29}H_{53}N_4O_9$
Exact Mass: 601.3813
Sample 4 (5 mer)
Structure:
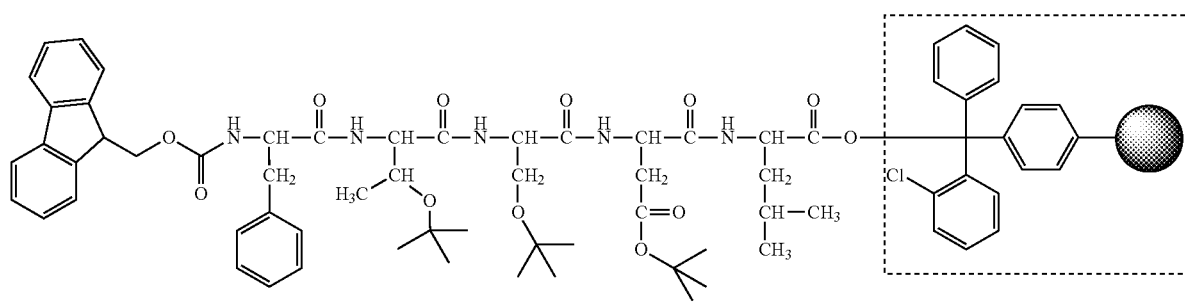
Chemical Formula: $C_{53}H_{72}N_5O_{12}$
Exact Mass: 970.5177
Sample 5 (5 mer de-Fmoc)
Structure:
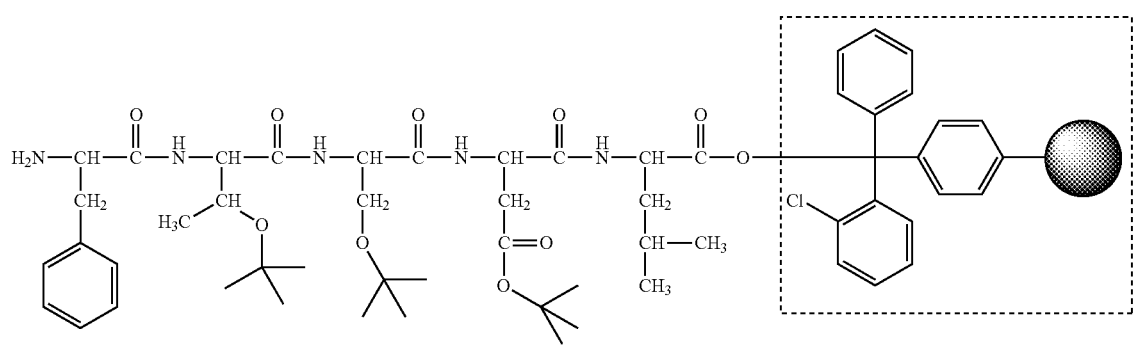
Chemical Formula: $C_{38}H_{62}N_5O_{10}$
Exact Mass: 748.4497

Sample 6 (6 mer)
Structure:

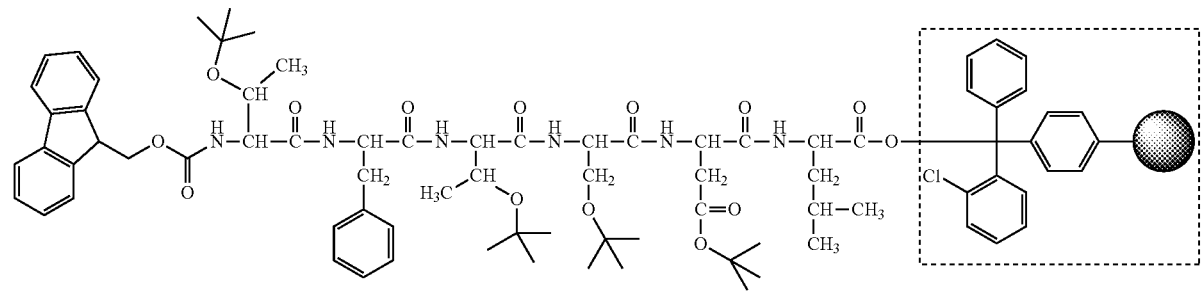

Chemical Formula: $C_{61}H_{87}N_6O_{14}$
Exact Mass: 1127.6280

Example 2

Figure 9:
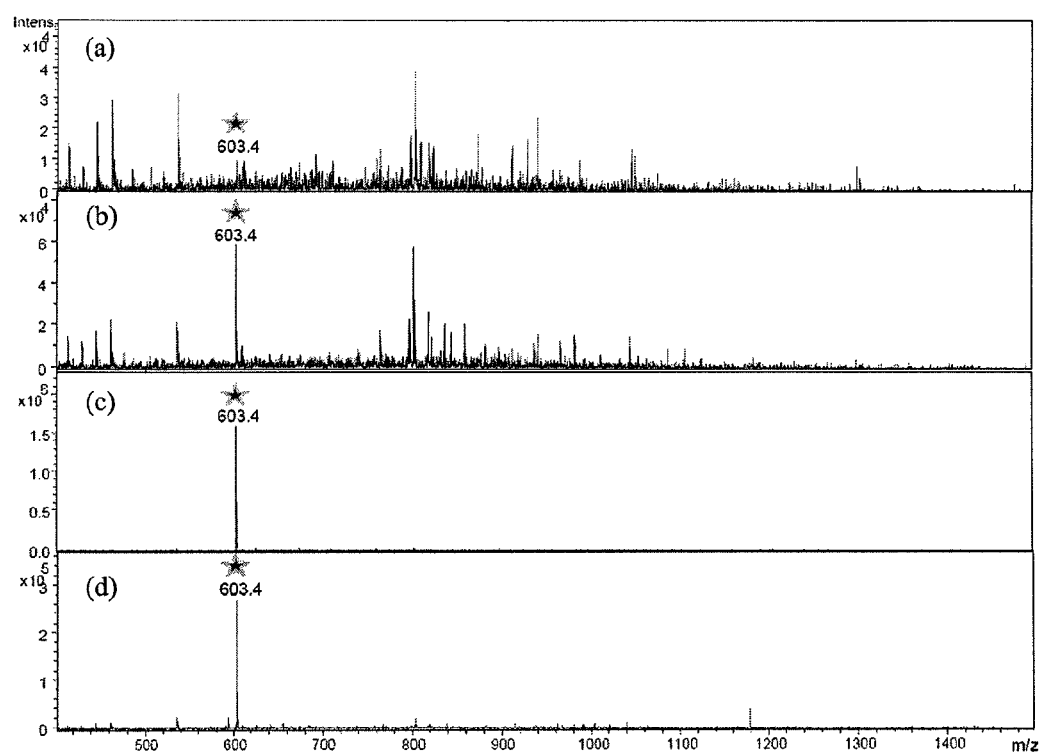
FIG. 9 provides a mass spectrum of 4mer de-Fmoc (m/z 603.3) peptide loaded onto four (4) sample plate materials, including (a) cotton sheet, (b) white polyethylene terephthalate, (c) steel and (d) black polyethylene terephthalate.

Sample plate material used for loading solid sample was found to influence the analytical stability and sensitivity of laser desorption and electrospray ionization mass spectrometry. FIG. 9 shows that sample 3 (4mer de-Fmoc, m/z 603.3) on resin peptide is used to demonstrate the sensitivities of four (4) plate materials, including cotton sheet, white polyethylene terephthalate, steel and black polyethylene terephthalate. The results show that the higher sensitivity is observed when sample loading on steel or black polyethylene terephthalate.

Figure 10:
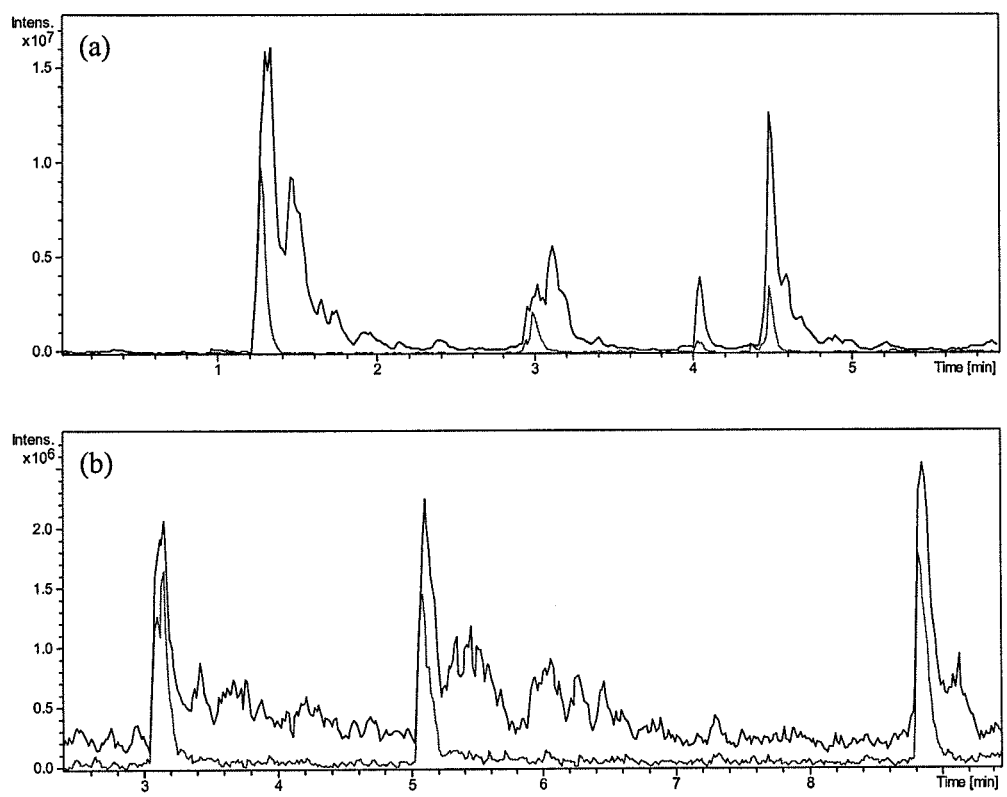
FIG. 10 provides a mass EIC (Extracted Ion Chromatogram) spectrum for stability of using different sample plate materials by using 5mer (m/z 972.5, red line) and 5mer de-Fmoc (m/z 750.4, blue line) peptide on resin as examples. (a) Steel sample plate. (b) Black polyethylene terephthalate.
Figure 11:
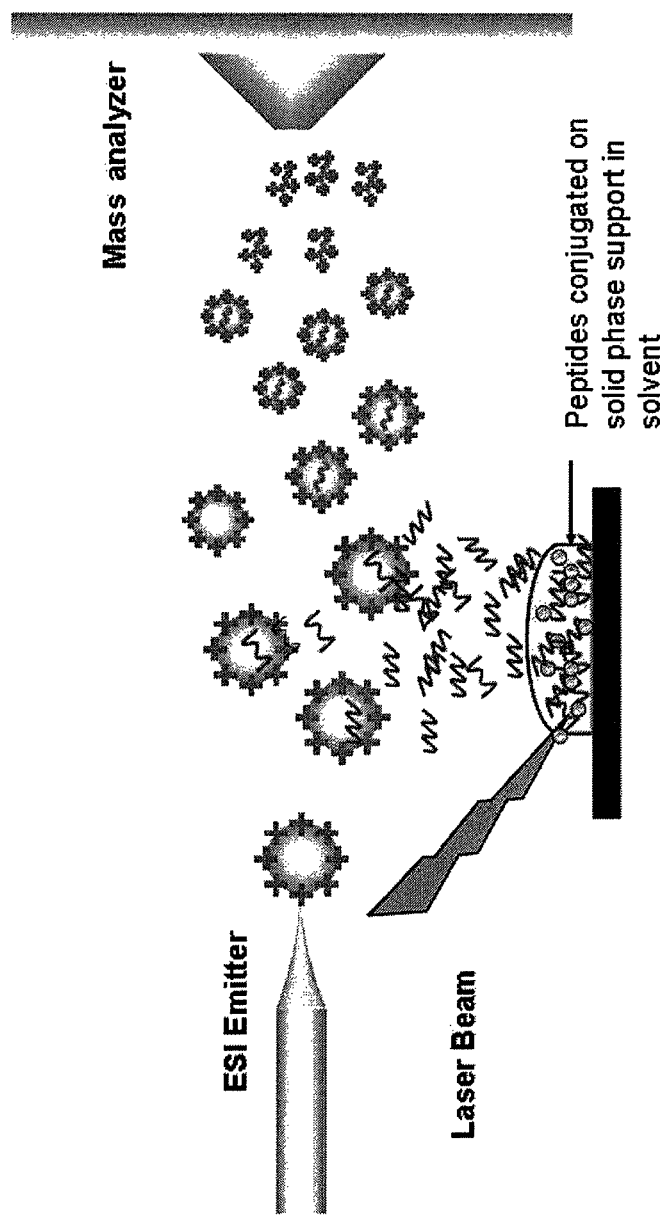
FIG. 11 provides an illustration of the present disclosure in which a support-bound sample is minimally disrupted with a laser beam to provide reaction product molecules that can be analyzed in the stream of an ESI emitter, using a mass analyzer.

Additionally, sample 4 (5 mer, m/z 972.5) and sample 5 (5 mer de-Fmoc, m/z 750.4) peptide on resin are used to demonstrate the analytical stability of steel and black polyethylene terephthalate. In FIG. 10, sample loading on black polyethylene terephthalate shows higher stability than loading on steel by triple repeats. Therefore, sample plate material can influence the analytical sensitivity and stability.

What is claimed is:

1. A method for real-time monitoring of a chemical reaction using a mass spectrometer, said method comprising the steps of:
   a) providing a synthesized sample bonded to a solid phase synthesis support in/from a container where the chemical synthesis occurs;
   b) subjecting the synthesized sample on a plate to an organic solvent;
   c) using a light source to break the chemical bond directly between the sample and solid phase synthesis support to which it is attached and transport the analyte molecules in an electrospray ionization plume; and
   d) analyzing the precursor ion spectrum of the analyte molecules to determine the molecular weight of synthesis products.

2. A method of claim 1, wherein the chemical reaction is peptide synthesis.

3. A method of claim 2, wherein the said peptide synthesis is solid phase peptide synthesis.

4. A method of claim 1, wherein the organic solvent is selected from dichloromethane or methanol.

5. A method of claim 4, wherein the organic solvent is selected from dichloromethane.

6. A method of claim 1, wherein the plate is selected from steel or polyester.

7. A method of claim 6, wherein the polyester is selected from polyethylene terephthalate.

8. A method of claim 7, wherein polyethylene terephthalate is black.

9. A method for real-time monitoring of solid phase peptide synthesis using a mass spectrometer, said method comprising the steps of:
   a) providing a peptide bonded directly to a solid phase peptide synthesis support in/from a container where the chemical synthesis occurs;
   b) subjecting the synthesized peptide on a plate to an organic solvent;
   c) using a light source to break the chemical bond directly between the sample and solid phase peptide synthesis support to which it is attached and transport the analyte molecules in an electrospray ionization plume; and
   d) analyzing the precursor ion spectrum of the analyte molecules to determine the molecular weight of synthesis products.

10. A method of claim 9, wherein the organic solvent is selected from dichloromethane.

11. A method of claim 9, wherein the plate is selected from steel or polyester.

12. A method of claim 11, wherein the polyester is selected from polyethylene terephthalate.

13. A method of claim 12, wherein the polyethylene terephthalate is black.

14. A method of claim 1, wherein the real-time monitoring of a chemical reaction is performed in a system comprising:
   a) a sample;
   b) a solvent exchange reservoir;
   c) a light source;
   d) an electrospray unit, and
   e) a mass spectrometer.

15. A method of claim 14, wherein the said sample is in/from a chemical synthesis reactor.

16. A method of claim 15, wherein the said chemical synthesis is peptide synthesis.

17. A method of claim 16, wherein said peptide synthesis is solid phase peptide synthesis.

* * * * *